US00PP08501P

United States Patent [19]

Imazio

[11] Patent Number: Plant 8,501

[45] Date of Patent: Dec. 14, 1993

[54] HEATHER PLANT NAMED ERICA PERSOLUTA FLAME

[75] Inventor: Bruno L. Imazio, Watsonville, Calif.

[73] Assignee: Imazio Nursery, Inc., Watsonville, Calif.

[21] Appl. No.: 984,470

[22] Filed: Dec. 2, 1992

[51] Int. Cl.[5] ..... A01H 5/00
[52] U.S. Cl. ..... Plt./54.1
[58] Field of Search ..... Plt./54.1

[56] References Cited

U.S. PATENT DOCUMENTS

P.P. 5,336 11/1984 Imazio ..... Plt. 54.1

*Primary Examiner*—James R. Feyrer
*Assistant Examiner*—Bruce R. Campell
*Attorney, Agent, or Firm*—Christie, Parker & Hale

[57] ABSTRACT

The present invention relates to a new and distinct cultivar of heather plant named 'Erica Persoluta Flame' having a comparatively early blooming habit and producing flowers of attractive magenta color on long stems.

4 Drawing Sheets

SUMMARY OF THE INVENTITON

The invention relates to a new and distinct variety of Ericaceae. The varietal denomination of the new variety is 'Erica Persoluta Flame'. The commercial name of the new variety is 'Sunset Flame'.

This new heather variety was discovered by me from among thousands of self-pollinated and/or naturally cross-pollinated seedlings growing in a controlled cultivated field of the variety 'Sunset' (U.S. Plant Pat. No. 5,336) in my commercial nursery at Watsonville, Calif. 'Sunset' is believed to be the seed parent of the new variety but the pollen parent is unknown. About 22,000 of these seedlings were dug up, potted and placed in a lath-house and by August of the same year, the healthiest survivors of the seedlings were planted in a controlled field by themselves.

The new variety was selected because of its good flower length and color, and especially, early blooming time. In particular, 'Erica Persoluta Flame' exhibits good stem length and shape and flowers of a beautiful vibrant magenta color. In 1986, 'Erica Persoluta Flame' bloomed in early October, when no other cultivated heather was available. Asexual reproduction from cuttings of the new variety, performed at the above noted location, has established that the combination of characteristics is retained through successive propagations.

Comparison With Closest Variety

The closest commercial cultivar to the new variety of which I am aware is the seed parent, 'Sunset' (U.S. Plant Pat. No. 5,336). 'Erica Persoluta Flame' resembles 'Sunset' in the color (dark green) and shape of the foliage and the color of the bloom (red-purple or magenta). The characteristics which distinguish the new variety from its seed parent are:

1. Blooming begins at least eight weeks before 'Sunset' blooms under normal circumstances. In most seasons this is October for the new variety and December for 'Sunset'.
2. The shape of the 'Erica Persoluta Flame' plant is much wider and more spread-out than that of the 'Sunset', which is more upright and narrow.
3. The branches of the new variety also exhibit this characteristic fullness, 'Erica Persoluta Flame' being wide and bushy at the base, whereas 'Sunset' is narrow and slender.

BRIEF DESCRIPTION OF THE ILLUSTRATIONS

The accompanying illustrations show the new variety in comparison to its closest known commercial variety and seed parent, 'Sunset', and to the seed parent of 'Sunset', the Erica persoluta.

Figure 1:
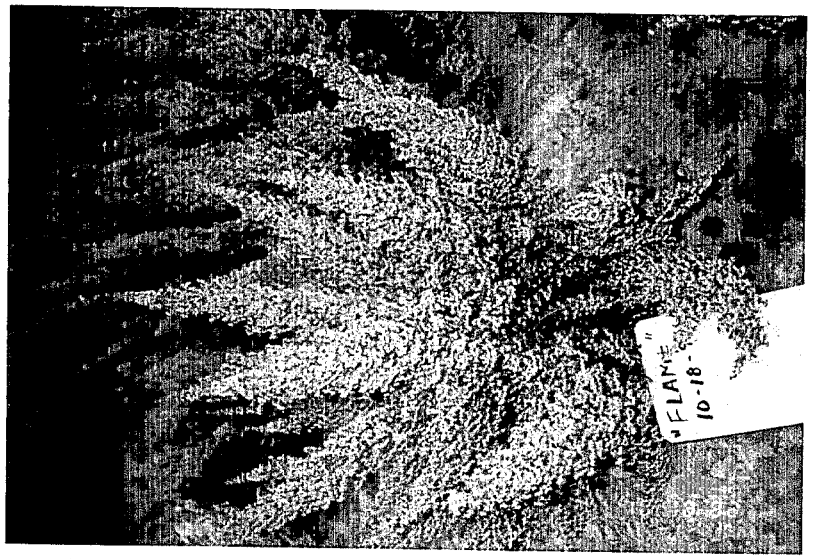
FIG. 1 is an illustration of the new variety illustrating the fullness of the branches and the plant.
Figure 2:
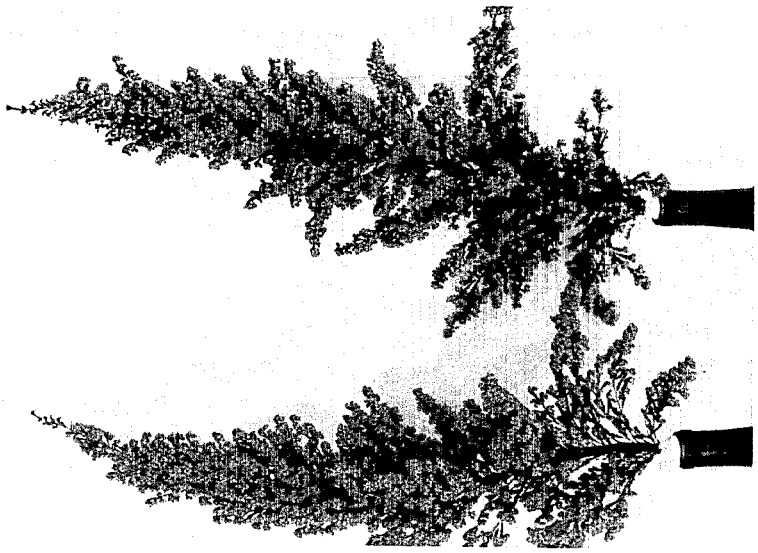
FIG. 2 shows two branches cut from a plant of 'Erica Persoluta Flame' and illustrates the overall shape and fullness of the branches and the woodiness of the main stem.
Figure 4:
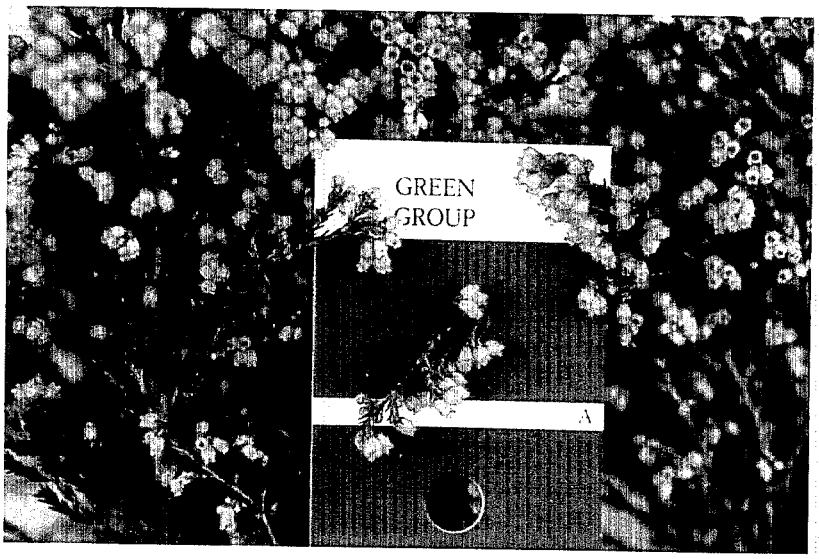
FIG. 4 is a color illustration of the blooms and also shows the shape of the foliage.
Figure 3:
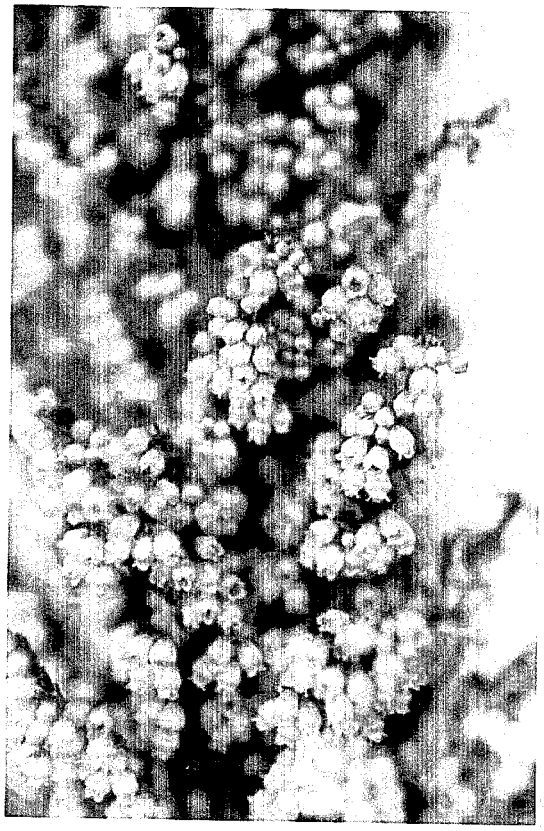
FIG. 3 is a closeup of one branch, giving a clear view of the shape, texture and density of the blooms and how they are borne.
Figure 6:
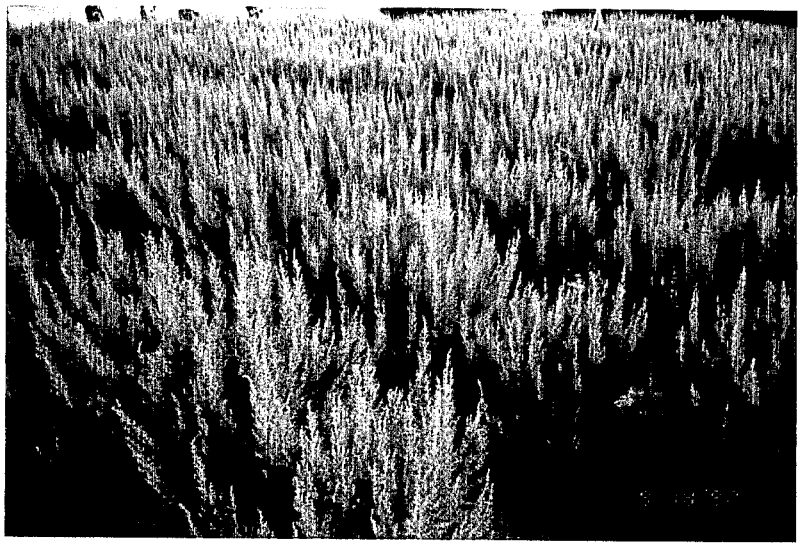
Figure 5:
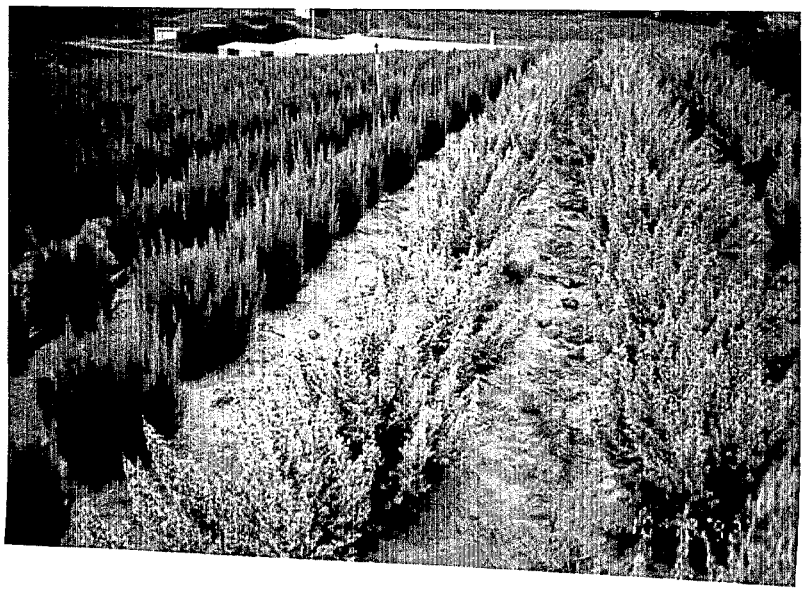
FIG. 5 is an illustration showing a field of fully bloomed plants of the new variety.
Figure 7:
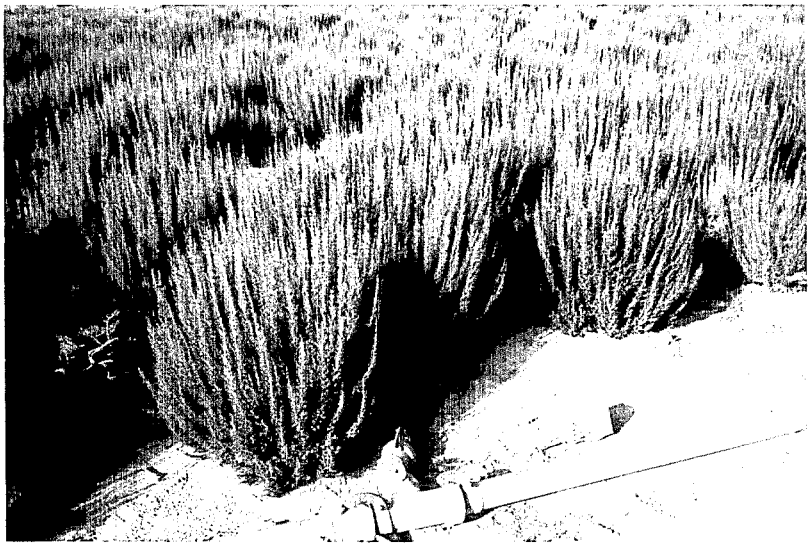

FIG. 6 is an illustration of plants of the new variety about one month prior to the fully blooming stage; and FIG. 7 is an illustration of 'Sunset' heather and serves to illustrate the contrasting shape of the seed parent, 'Sunset', the closest commercial cultivar to the new variety, and also shows the difference between the blooming times of the new variety and 'Sunset'. 'Sunset' is still green with no blooms while the new variety is in full bloom.

DETAILED DESCRIPTION OF THE NEW VARIETY

The following is a detailed description of 'Erica Persoluta Flame' based upon observation of field-grown plants in September and October at Watsonville, Calif. The color terminology used is in accordance with The Royal Horticultural Society Colour Chart (RHSCC), the colors specified being as accurate as can be reasonably obtained in an illustration of this character. It is understood that phenotypic expression may vary depending on light availability, climate and cultural conditions.

Origin: Seedling.
Parentage:
*Seed parent.*—'Sunset'.
*Pollen parent.*—Unknown.

PLANT

Form: Woody shrub, perennial.
Shape: Generally upright with stems curving to accommodate fullness of the plant, which is open, wide and bushy.
Height: 2½ to 3 feet at maturity.
Main stem length: 2 to 3 feet.
Branching: Thick, woody branches widely spaced due to fullness.
Growth: Vigorous, flexible wood.
Foliage:
*Size of leaf.*—About ⅛ inch long.
*Shape.*—Very narrow, about 1/16 inch or less.
*Color.*—Dark yellowish-green, near 141A.
*Texture.*—Smooth.
Effects of weather: Plant can tolerate freezing temperatures for several hours. Temperatures over 90° F. stress the plant. Warm temperatures hasten bud formation and blooming. Extended wet weather causes flowers to decline more rapidly when in full bloom.

BUD

Size: About ⅛ inch or less in diameter, approximately ⅜ inch or less in length.
Shape: Globose urceolate.
Color: Red-violet or magenta, near 70A.
Rate of opening: Progressive and rapid from base of plant upwards to tip.

INFLORESCENCE

Blooming habit: Once annually, usually beginning late September/early October in Watsonville, Calif. and continuing for several weeks.
Size of bloom: About ⅜ inch long, about ⅛ inch diameter.
Borne: Compound raceme with terminal clusters.
Shape: Globose urceolate.
Appearance: Satiny.
Color: Red-violet or magenta, near 70A.
Flower stem:
*Length.*—About ¼ to 4 inches (these are the side branches bearing the blooms).
*Color.*—Light brown.
*Strength.*—Supple.
Fragrance: Pungent-sweet.
Lasting quality:
*On plant.*—About 6 to 8 weeks.
*As cut flower.*—Up to 4 weeks.
Discoloration: Can fade slightly in long exposure to bright sun
Persistence: Blooms can persist long after stem ceases to draw water. Blooms persist on plant for extended period and turn brown.

I claim:

1. A new and distinct cultivar of heather plant, substantially as herein shown and described, characterized by its early blooming habit relative to its seed parent, 'Sunset', and by its rich magenta color and tall, bushy stems.

* * * * *